(12) United States Patent
Rehbein et al.

(10) Patent No.: US 11,865,313 B2
(45) Date of Patent: *Jan. 9, 2024

(54) DATA COLLECTION APPARATUS FOR ATTACHMENT TO AN INJECTION DEVICE

(71) Applicant: Sanofi-Aventis Deutschland GMBH, Frankfurt am Main (DE)

(72) Inventors: Christian Rehbein, Frankfurt am Main (DE); Sven Hagebusch, Frankfurt am Main (DE); Chris Knorr, Frankfurt am Main (DE); Maurice Toporek, Frankfurt am Main (DE); Matthias Felber, Frankfurt am Main (DE); Alexander Heinrich, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 133 days.

This patent is subject to a terminal disclaimer.

(21) Appl. No.: 17/450,849

(22) Filed: Oct. 14, 2021

(65) Prior Publication Data

US 2022/0031958 A1 Feb. 3, 2022

Related U.S. Application Data

(63) Continuation of application No. 17/133,149, filed on Dec. 23, 2020, which is a continuation of application
(Continued)

(30) Foreign Application Priority Data

Sep. 9, 2016 (EP) ..................................... 16188182

(51) Int. Cl.
*A61M 5/31* (2006.01)
*A61M 5/315* (2006.01)
(Continued)

(52) U.S. Cl.
CPC ............ *A61M 5/3155* (2013.01); *A61M 5/20* (2013.01); *A61M 5/31585* (2013.01);
(Continued)

(58) Field of Classification Search
CPC .. A61M 2005/3126; A61M 2205/3313; A61M 5/3155
See application file for complete search history.

(56) References Cited

U.S. PATENT DOCUMENTS 10,420,895 B2 9/2019 Erbstein et al.
11,547,806 B2 * 1/2023 Rehbein .............. A61M 5/3155
(Continued)

FOREIGN PATENT DOCUMENTS

CN 102458523 5/2012
CN 104936640 9/2015
(Continued)

OTHER PUBLICATIONS

International Preliminary Report on Patentability in Application No. PCT/EP2017/072618, dated Mar. 12, 2019, 7 pages.
(Continued)

*Primary Examiner* — William R Carpenter
(74) *Attorney, Agent, or Firm* — Fish & Richardson P.C.

(57) ABSTRACT

A data collection device including an attachment assembly for attaching the data collection device to a dose setting dial of a medicament administration device, a light source configured to illuminate a portion of a surface of an internal component of the medicament administration device including a pattern of relatively reflective and non-reflecting regions formed on the surface of the internal component, and an optical sensor configured to receive light reflected by at least the relatively reflective regions.

24 Claims, 7 Drawing Sheets

Related U.S. Application Data

No. 16/331,656, filed as application No. PCT/EP2017/072618 on Sep. 8, 2017, now Pat. No. 11,547,806.

(51) Int. Cl.
*A61M 5/20* (2006.01)
*G16H 20/10* (2018.01)

(52) U.S. Cl.
CPC ..... *G16H 20/10* (2018.01); *A61M 2005/3126* (2013.01); *A61M 2205/3306* (2013.01); *A61M 2205/3313* (2013.01); *A61M 2205/3317* (2013.01); *A61M 2205/3327* (2013.01); *A61M 2205/3561* (2013.01); *A61M 2205/50* (2013.01); *A61M 2205/502* (2013.01); *A61M 2205/52* (2013.01); *A61M 2205/587* (2013.01)

(56) References Cited

U.S. PATENT DOCUMENTS

| | | | |
|---|---|---|---|
| 2011/0190693 | A1 | 8/2011 | Takatsuka et al. |
| 2011/0270214 | A1 | 11/2011 | Jorgensen et al. |
| 2013/0197445 | A1 | 8/2013 | Schabbach et al. |
| 2013/0310756 | A1 | 11/2013 | Whalley et al. |
| 2015/0202375 | A1 | 7/2015 | Schabbach et al. |
| 2016/0015902 | A1 | 1/2016 | Draper |
| 2017/0138769 | A1 | 5/2017 | Jones et al. |
| 2018/0221587 | A1 | 8/2018 | Keitel |

FOREIGN PATENT DOCUMENTS

| | | |
|---|---|---|
| CN | 104981262 | 10/2015 |
| CN | 105120928 | 12/2015 |
| CN | 105307711 | 2/2016 |
| CN | 105324142 | 2/2016 |
| CN | 105611959 | 5/2016 |
| CN | 105771039 | 7/2016 |
| DE | 202015006845 | 1/2016 |
| EP | 1776975 | 4/2007 |
| JP | 2015-518747 | 7/2015 |
| JP | 2016-506845 | 3/2016 |
| JP | 2017-520303 | 7/2017 |
| JP | 2018-505007 | 2/2018 |
| JP | 2018-517502 | 7/2018 |
| WO | WO 2010/139671 | 12/2010 |
| WO | WO 2012/046199 | 4/2012 |
| WO | WO 2012/158138 | 11/2012 |
| WO | WO 2013/010889 | 1/2013 |
| WO | WO 2013/098421 | 7/2013 |
| WO | WO 2013/177135 | 11/2013 |
| WO | WO 2014/108551 | 7/2014 |
| WO | WO 2014/111341 | 7/2014 |
| WO | WO 2014/128156 | 8/2014 |
| WO | WO 2014/128157 | 8/2014 |
| WO | WO 2014/173434 | 10/2014 |
| WO | WO 2014/173770 | 10/2014 |
| WO | WO 2014/180745 | 11/2014 |
| WO | WO 2015/055640 | 4/2015 |
| WO | WO 2015/185687 | 12/2015 |
| WO | WO 2016/131713 | 8/2016 |
| WO | WO 2016/198516 | 12/2016 |

OTHER PUBLICATIONS

International Search Report and Written Opinion in Application No. PCT/EP2017/072618, dated Nov. 22, 2017, 10 pages.

* cited by examiner

DATA COLLECTION APPARATUS FOR ATTACHMENT TO AN INJECTION DEVICE

CROSS REFERENCE TO RELATED APPLICATIONS

The present application is a continuation of U.S. application Ser. No. 17/133,149, filed on Dec. 23, 2020, which is a continuation application of U.S. application Ser. No. 16/331,656, filed on Mar. 8, 2019, which is the national stage entry of International Patent Application No. PCT/EP2017/072618, filed on Sep. 8, 2017, and claims priority to Application No. EP 16188182.6, filed on Sep. 9, 2016, the disclosures of which are incorporated herein by reference.

TECHNICAL FIELD

The present disclosure relates to a data collection device for attachment to an injection device and collecting medicament dosage information therefrom.

BACKGROUND

A variety of diseases exists that may require regular treatment by injection of a medicament. Such injection can be performed by using injection devices, which are applied either by medical personnel or by patients themselves. As an example, type-1 and type-2 diabetes can be treated by patients themselves by injection of insulin doses, for example once or several times per day. For instance, a pre-filled disposable insulin pen can be used as an injection device. Alternatively, a re-usable pen may be used. A re-usable pen allows replacement of an empty medicament cartridge by a new one. Either pen may come with a set of one-way needles that are replaced before each use. The insulin dose to be injected can then for instance be manually selected at the insulin pen by turning a dosage knob and observing the actual dose from a dose window or display of the insulin pen. The dose is then injected by inserting the needle into a suited skin portion and pressing the dosage knob or an injection button of the insulin pen.

SUMMARY

A first aspect provides a data collection device. The device includes an attachment assembly for attaching the data collection device to a dose setting dial of a medicament administration device.

The device includes a light source configured to illuminate a portion of a surface of an internal component of the medicament administration device including a pattern of relatively reflective and non-reflecting regions formed on the surface of the internal component. The device includes an optical sensor configured to receive light reflected by at least the relatively reflective regions.

A second aspect provides a system. The system includes a medicament administration device. The medicament administration device includes a dose setting dial. The medicament administration device includes an internal component that rotates around a longitudinal axis of the device when a dose of medicament is delivered from the device. The internal component includes a pattern of relatively reflective and non-reflecting regions formed on a surface thereof, and the data collection device according to the first aspect.

A third aspect provides a system. The system includes a medicament administration device. The medicament administration device includes a dose setting dial. The medicament administration device includes an internal component that rotates around a longitudinal axis of the device when a dose of medicament is delivered from the device. The internal component includes a pattern of relatively reflective and non-reflecting regions formed on a surface thereof, and a data collection device comprising. The data collection device includes an attachment assembly for attaching the data collection device to the dose setting dial, a light source configured to illuminate a portion of the surface of the internal component including the pattern of relatively reflective and non-reflecting regions, and an optical sensor configured to receive light reflected by at least the relatively reflective regions.

The light source and the optical sensor can be supported on a side of the data collection device which abuts the dose setting dial of the drug delivery device. The attachment assembly can be configured to releasably attach the data collection device to the dose setting dial of the medicament administration device such that the dose setting dial of the medicament administration device is disposed in a light path between the light source, portion of the surface of the internal component and optical sensor.

The light source and optical sensor can be located proximally of the dose setting dial when the data collection device is attached to the dose setting dial such that the light path between the light source, internal component and optical sensor passes through a proximal end surface of the dose setting dial. The light source and optical sensor can be located between the attachment assembly and the dose setting dial when the data collection device is attached to the dose setting dial such that the light path between the light source, internal component and optical sensor passes through a side surface of the dose setting dial.

The dose setting dial of the medicament administration device can be at least partially transmissive to electromagnetic radiation emitting by the light source. The electromagnetic radiation can be Infrared light.

The data collection device of the first or second aspect can include an electronics assembly including the light source and the optical sensor. The electronics assembly can be configured to move longitudinally relative to the attachment assembly. The dose setting dial of the medicament administration device can include a dose delivery button. The electronics assembly can be configured to abut the dose delivery button when the data collection device is attached to the dose setting dial and to cause depression of the dose delivery button when the electronics assembly is moved longitudinally in a distal direction relative to the attachment assembly.

The light source and optical sensor can be located proximally of the dose delivery button when the data collection device is attached to the dose setting dial such that the light path between the light source, internal component and optical sensor passes through the dose delivery button. The light source and optical sensor can be located on an underside of the electronics assembly.

The pattern of relatively reflective and non-reflecting regions can include evenly spaced relatively reflective and non-reflecting regions formed on a proximal end surface of the internal component.

The light source and optical sensor can be located between the attachment assembly and the dose setting dial when the data collection device is attached to the dose setting dial such that the light path between the light source, internal component and optical sensor passes through the dose setting dial. The light path between the light source, internal component and optical sensor can pass through a part of the dose delivery button.

The pattern of relatively reflective and non-reflecting regions can include evenly spaced relatively reflective and non-reflecting regions formed on an outer circumferential surface of the internal component.

The data collection device of the first or second aspect can include an electronics assembly including the light source and the optical sensor. The electronics assembly and the attachment assembly can be fixedly connected together. The electronics assembly can be configured to abut a proximal end surface of the dose setting dial when the data collection device is attached to the dose setting dial. The electronics assembly can be configured to abut a circumferential surface of the dose setting dial when the data collection device is attached to the dose setting dial.

The light source and optical sensor can be located proximally of the dose setting dial when the data collection device is attached to the dose setting dial such that the light path between the light source, internal component and optical sensor passes through the dose setting dial. The light source and optical sensor can be located on an underside of the electronics assembly.

The light source and optical sensor can be located between the attachment assembly and the dose setting dial when the data collection device is attached to the dose setting dial such that the light path between the light source, internal component and optical sensor passes through the dose setting dial.

The data collection device of the first or second aspects can include a processor arrangement configured to receive signals from the optical sensor and to detect the occurrence of a medicament delivery from the medicament administration device. The processor arrangement can be configured to determine, from the signals received from the optical sensor, an amount of rotation of the internal component.

The data collection device of the first or second aspect can include a switch configured to be triggered by application of a force to a proximal end of the data collection device and wherein triggering of the switch may be configured to cause activation of at least the light source, optical sensor and processor arrangement. The switch can be a mechanical switch. The switch can be an optical wake-up sensor configured to sense the reflectance and/or colour of an underlying component of the medicament administration device and to provide a wake-up signal when a change in the reflectance and/or colour is detected.

The data collection device of the first or second aspect can include a timer and the switch can be further configured to trigger activation of the timer. The data collection device of the first or second aspect can be further configured to determine an elapsed time since the timer was last triggered and to generate an alert if the elapsed time is inconsistent with a threshold condition.

The processor arrangement can be configured to determine a time stamp for the administration of the medicament dosage using said timer and to store the determined medicament dosage and said time stamp. The processor arrangement can be configured to transmit a log of determined internal component rotation angles and time stamp information to another device.

The medicament administration device can include a housing and the dose setting dial does not rotate relative to the housing when a dose of medicament is delivered from the device. The internal component can include a number of equally spaced crenellations and wherein the relatively reflective regions may be formed on the upper surfaces of the crenellations. The light source can be an infrared light source and components of the medicament administration device disposed in the light path between the light source and the optical sensor can be completely or partially transmissive to infrared light. The processor arrangement can be configured to detect the occurrence of two separate medicament deliveries and to amalgamate the two medicament deliveries when it is determined that the two deliveries occurred within a predetermined time of each other.

A fourth aspect provides a data collection device releasably attachable to a medicament administration device. The data collection device includes a sensor arrangement adapted to detect signals related to a dose amount and generated during dose dialing and/or dose ejection from said medicament administration device, and a processor adapted to determine dose amounts or rotation angels based on the detected signals. The data collection device is designed to be attachable to a dose selection element of said medicament administration device and the sensor arrangement is supported on an inner surface of a mounting component of said data collection device facing the dose selection element when attached to said medicament administration device.

In general, any component which is located close to the dose setting dial and which rotates when a dose is dispensed from the injection device can be used as the internal component having the pattern of relatively reflective and non-reflective regions formed on a surface thereof. Certain embodiments describe a data collection device having a light source and sensor arrangement configured to abut the dose dial (including a release button if present) when attached to an injection device. The light source and sensor are configured to emit and detect radiation that can pass through material without requiring a cutout, aperture or the like, thus preventing ingress of dirt. One example for the suitable radiation is Infrared light.

A fifth aspect provides a data collection device. The device includes an attachment assembly for attaching the data collection device to a dose setting dial of a medicament administration device, and an electronics assembly comprising a non-contact sensor configured to detect rotation of an internal component of the medicament administration device. The internal component is configured to rotate when a dose is delivered from the medicament administration device.

The internal component of the medicament administration device can include one or more magnets or magnetic areas and the non-contact sensor may be a magnetic sensor configured to detect a change in a magnetic field when the internal component is rotated.

BRIEF DESCRIPTION OF THE DRAWINGS

Example embodiments will now be described with reference to the accompanying figures, of which.

DETAILED DESCRIPTION

In the following disclosure, embodiments will be described with reference to an insulin injection device. The present disclosure is however not limited to such application and may equally well be deployed with injection devices that eject other medicaments.

Figure 1:
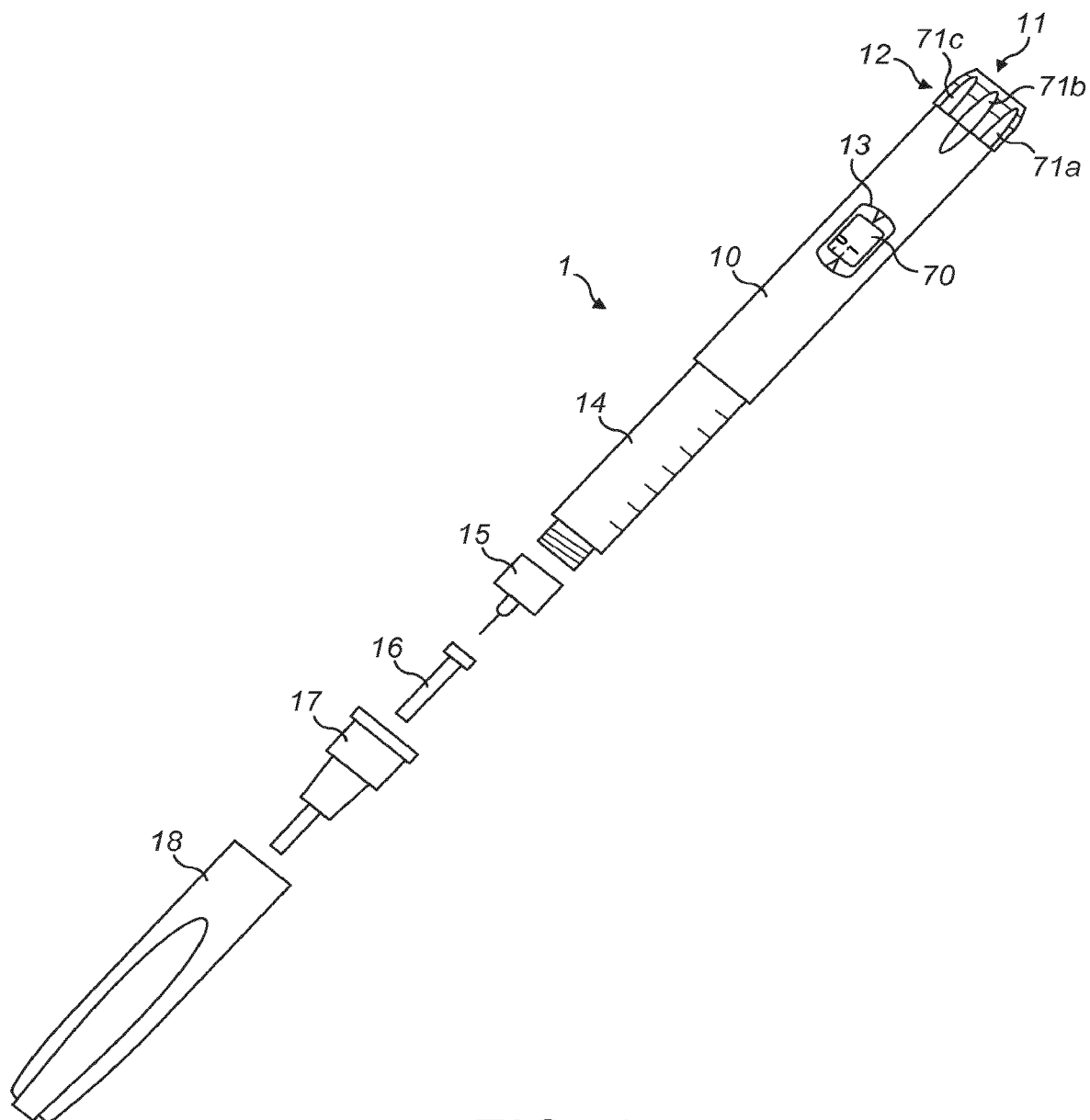
FIG. 1 shows an exploded view of an injection device for use with a data collection device.

FIG. 1 is an exploded view of a medicament administration device. In this example, the medicament administration device is an injection device 1, such as Sanofi's AllStar® insulin injection pen, however the present invention is also compatible with other types and makes of injection pens as described below.

The injection device 1 of FIG. 1 is a pre-filled injection pen that comprises a housing 10 and contains an insulin container 14, to which a needle 15 can be affixed. The injection device 1 may be disposable or re-usable. The needle is protected by an inner needle cap 16 and either an outer needle cap 17 or an alternative cap 18. An insulin dose to be ejected from injection device 1 can be programmed, or 'dialled in' by turning a dosage knob 12 (also referred to herein as a dose selection element 12), and a currently programmed dose is then displayed via dosage window 13, for instance in multiples of units. For example, where the injection device 1 is configured to administer human insulin, the dosage may be displayed in so-called International Units (IU), wherein one IU is the biological equivalent of about 45.5 micrograms of pure crystalline insulin (1/22 mg). Other units may be employed in injection devices for delivering analogue insulin or other medicaments. It should be noted that the selected dose may equally well be displayed differently than as shown in the dosage window 13 in FIG. 1.

The dosage window 13 can be in the form of an aperture in the housing 10, which permits a user to view a limited portion of a number sleeve 70 that is configured to move when the dosage knob 12 is turned, to provide a visual indication of a currently programmed dose. Alternatively, the number sleeve 70 can remain stationary during the dose dialling phase, and the dosage window 13 may move as a dose is dialled in to reveal the number corresponding to the dialled dose. In either case, the number sleeve 70 may be a component which rotates when a dose is being dispensed from the injection device 1.

In this example, the dosage knob 12 includes one or more formations 71a, 71b, 71c that facilitate programming because they improve the grip a user feels when grasping the dosage knob 12. In another example (not shown) the dosage knob does not include formations.

Attaching a data collection device does not require the dosage knob having formations. Having a tight fit and/or using rubber-like material at the contact surface between the data collection device and the injection device can provide an attachment that, on the one hand, facilitates a stable connection in the sense that the two devices remain attached to each other and, on the other hand, allows the two devices to be separated when intended. The rubber-like material would ensure a proper fit even on a smooth surface, e. g, a dosage knob having a smooth surface such that that rotation of the data collection device causes rotation of the dosage knob and vice versa.

The injection device 1 can be configured so that turning the dosage knob 12 causes a mechanical click sound to provide acoustical feedback to a user. The number sleeve 70 mechanically interacts with a piston in insulin container 14. When needle 15 is stuck into a skin portion of a patient, and then injection button 11 is pushed, the insulin dose displayed in display window 13 will be ejected from injection device 1. When the needle 15 of injection device 1 remains for a certain time in the skin portion after the injection button 11 is pushed, a high percentage of the dose can be injected into the patient's body. Ejection of the insulin dose can also cause a mechanical click sound, which is however different from the sounds produced when using dosage knob 12. In some other embodiments, the injection device 1 does not have a separate injection button 11 and a user depressed the entire dosage knob 12, which moves longitudinally relative to the housing 10, in order to cause the medicament to be dispensed.

In the various embodiments, during delivery of the insulin dose, the dosage knob 12 is turned to its initial position in an axial movement, that is to say without rotation, while the number sleeve 70 is rotated to return to its initial position, e.g. to display a dose of zero units.

Injection device 1 can be used for several injection processes until either the insulin container 14 is empty or the expiration date of the medicament in the injection device 1 (e.g. 28 days after the first use) is reached.

Furthermore, before using injection device 1 for the first time, it may be necessary to perform a so-called "prime shot" to remove air from insulin container 14 and needle 15, for instance by selecting two units of insulin and pressing injection button 11 while holding injection device 1 with the needle 15 upwards. For simplicity of presentation, in the following, it will be assumed that the ejected amounts substantially correspond to the injected doses, so that, for instance the amount of medicament ejected from the injection device 1 is equal to the dose received by the user. Nevertheless, differences (e.g. losses) between the ejected amounts and the injected doses may need to be taken into account.

Figure 2:
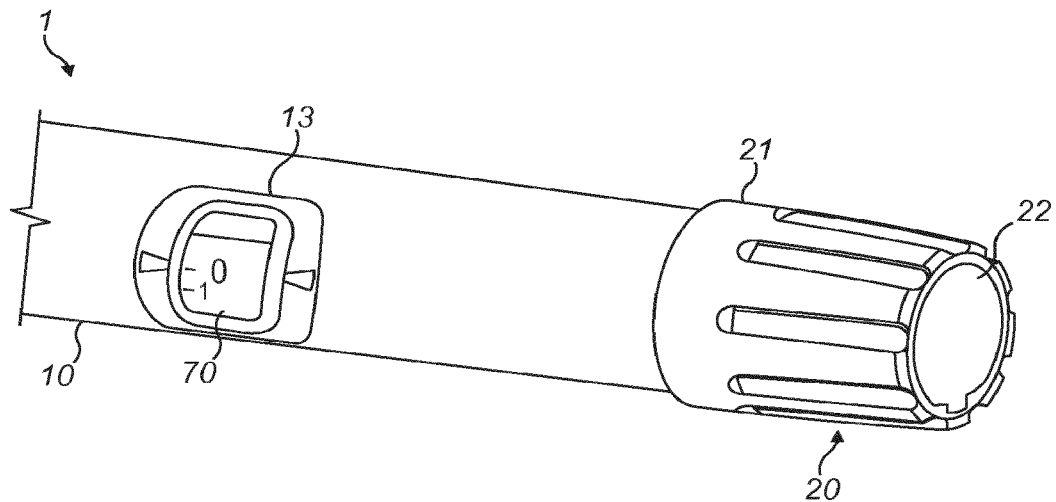
FIG. 2 depicts a data collection device, attached to the injection device of FIG. 1.

FIG. 2 is a perspective view of one end of the injection device 1 when a data collection device 20 according to an example embodiment is attached. The data collection device 20 includes a housing 21 with an end plate 22 forming a user interaction surface. The housing 21 can support an optical user feedback such as one or more LEDs (not shown). In some optional embodiments, the data collection device 20 comprises a display (not shown). The data collection device 20 is compatible with a number of existing injection devices 1. The data collection device 20 is compatible with injection devices having a separate dose delivery button or an integrated dial. The data collection device 20 is compatible with injection devices where the dose setting dial does not rotate during dose administration, but where an internal component close to the dose setting dial does rotate during dose administration. The data collection device 20 allows the rotation of this internal component to be detected and measured.

Figure 3:
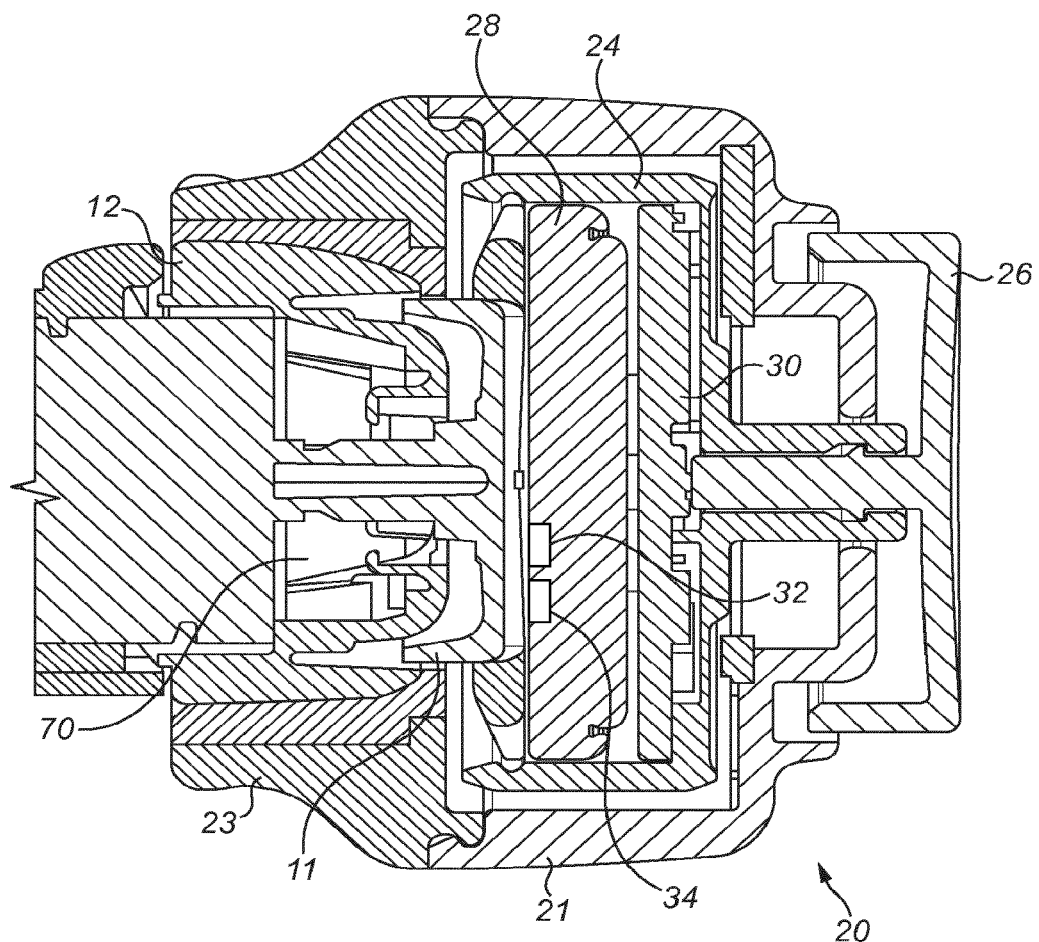
FIG. 3 is a cross-sectional view of a data collection device when attached to a first type of injection device.

FIG. 3 is a cross-sectional view of the data collection device 20 according to some embodiments, when attached to a first type of injection device 1.

In these embodiments, the injection device 1 is of a type having a dose setting dial 12 with a depressible dose delivery button 11, which a user would normally depress in order to activate the dispensing mechanism. The dose setting dial 12 is configured to be rotated to set a dose.

In some injection devices, rotation of the dose setting dial 12 causes an internal spring to be tensioned, or the device may have a pre-tensioned spring. In some implementations, the dose setting dial 12 does not move longitudinally during dose setting. The dose setting dial 12 remains stationary during dose dispensing. For some other injection devices rotation of the dose setting dial 12 also causes the dose setting dial to move proximally out of the housing 10. When a dose is dispensed from the injection device 1, the dose setting dial moves back (distally) into the housing, but does not rotate. In either case, an internal component 70, such as a number sleeve 70, rotates during dose dispense. The data collection device 20 is configured so as to detect and measure the rotation of this internal component 70 when attached to the injection device 1.

The data collection device 20 includes a housing 21, an electronics assembly 24 disposed inside the housing 21 and a button 26 which protrudes from the proximal end of the housing 21 and is moveable longitudinally with respect to the housing 21. The housing 21 includes an attachment assembly 23 configured to secure the data collection device 20 to the dose setting dial 12. The formations 71a, 71b, 71c on the dose setting dial 12 may be used to facilitate attachment of the data collection device 20.

In this particular example, the attachment assembly 23 is a sleeve that is positioned over the dose setting dial 12 through formations, not shown, that co-operate with the formations 71a, 71b, 71c on the dose setting dial 12 so that, when the dose setting dial 12 rotates during programming of the dosage, the data collection device 20 also rotates. Alternatively, or additionally, resilient padding, such as a foam rubber pad 44, can be provided within the formations on the attachment assembly 23, to allow for tolerances in the dimensions of the formations on the attachment assembly 23 and the formations 71a, 71b, 71c on the dose setting dial 12 and/or to provide an engagement between the attachment assembly 23 and the dose setting dial 12 so that rotation of the attachment assembly 23 causes rotation of the dose setting dial 12 and vice versa. In some implementations, the attachment assembly 23 includes a resilient padding of sufficient thickness to render formations that co-operate with the formations 71a, 71b, and 71c on the dose setting dial. The padding is soft enough to conform to the surface of the dose setting dial 12. For example, the padding is soft enough to conform to the formations on the surface of the dose setting dial 12.

The electronics assembly 24 is retained within the housing 21 such that it can move longitudinally with respect to the housing 21. The distal side of the electronics assembly 24 is configured to abut the dose delivery button 11 when the data collection device 20 is attached to the injection device. The proximal side of the electronics assembly 24 abuts or is integral with the button 26. The button 26 and electronics assembly 24 can form a single subassembly. The attachment assembly 23 can form another subassembly. In this embodiment the two subassemblies are able to move longitudinally relative to each other, but cannot rotate relate to each other. The button 26 provides the finger rest for the user and the push surface for transmitting a push force to the dose delivery button 11 of the injection device. The result of this configuration is that when the button 26 of the data collection device 20 is depressed, the force is transferred through the electronics assembly 24 to the dose delivery button 11, causing it to be depressed.

The electronics assembly 24 comprises a PCB 28 and a battery 30, for example in the form of a coin cell. The PCB 28 may support a number of components including a processor arrangement 50, a light source 32 and an optical sensor 34. In these embodiments, the light source 32 is an Infrared light source and the optical sensor 34 is an Infrared optical sensor. As shown in FIG. 3, in some embodiments, the light source 32 and optical sensor 34 are supported on the side of the PCB which abuts the dose delivery button 11. The dose delivery button 11 is transparent or substantially transparent to Infrared radiation. Thus the light emitted by the light source 32 passes through the dose delivery button 11 and illuminates the internal components. In particular the number sleeve 70 is a hollow cylinder which extends to the proximal end of the housing 10 and is releasably fixed to the dose setting dial 12. The annular end surface of the number sleeve 70 therefore sits underneath the dose delivery button 11 and is illuminated by the Infrared light. The number sleeve 70 is provided with a pattern of relatively reflective and non-reflective regions on the annular end surface. For example, equally spaced and equally sized reflective and non-reflective sections may be arranged alternately. During a dose dispensing operation, the light source 32 illuminates the part of the number sleeve 70 including the pattern of relatively reflective and non-reflecting regions; and the optical sensor 34 receives the light reflected by at least the relatively reflective regions. As the dose delivery button 11 is depressed by the electronics assembly 24 during dose dispensing, the distance (light path) between the light source 32 and optical sensor 34 is shorter than during dialing. The output of the optical sensor 34 is relayed to the processor 50 which calculates an amount of rotation of the number sleeve 70 during the dose dispensing operation. From the amount of rotation, the delivered dose can be calculated. This may be done by the data collection device 20 or by another computing device. In general, any component which is located close to the dose setting dial and which rotates when a dose is dispensed from the injection device 1 may be used as the internal component having the pattern of relatively reflective and non-reflective regions formed on a surface thereof.

Figure 4:
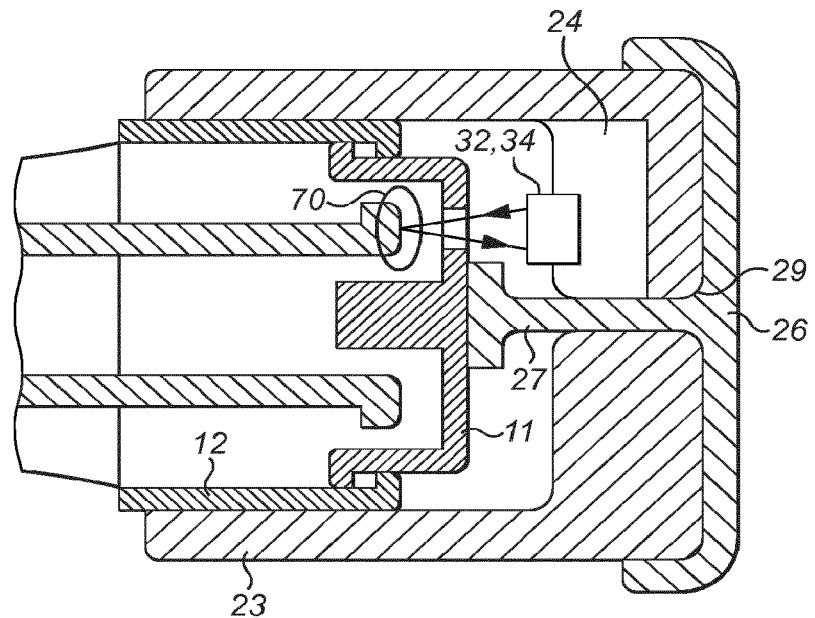
FIG. 4 illustrates an alternative arrangement for the components of a data collection device.

FIG. 4 illustrates an alternative arrangement for the components of the data collection device 20. In this embodiment, the electronics assembly is integral with or supported on an internal surface of the attachment assembly 23 and is configured to remain substantially stationary relative to the attachment assembly. The button 26 of the data collection device 20 has an elongate portion 27 which extends through an aperture 29 in the proximal end face of the data collection device. The elongate portion 27 is configured to contact the dose delivery button 11 of the injection device 1 and to transfer force form the button 26 to the dose delivery button 11. As in the previous embodiment, the light source 32 and optical sensor 34 are arranged so as to face the dose delivery button 11, which is partially or completely transparent to infrared radiation. The light path between the light source 32, reflective regions of the number sleeve 70 and optical sensor 34 may be extended in this embodiment and suitable optical elements may be employed to focus the light.

An advantage of the embodiment of FIG. 4 is the simple mechanical design and construction and that the subassembly (button 26) that transmits the push force to inject is minimized. This increases user comfort as friction is reduced and less mass needs to be moved by the user. As a result, triggering an injection requires a relatively small amount of additional force from the user.

An advantage of the embodiment of FIG. 3 is that the optical path is minimized when a dose detection is being performed, as the electronics assembly 24 directly abuts the dose delivery button 11. The optical path in FIG. 3 may be reduced with respect to the optical path in FIG. 4 (in which the electronics assembly is integral with or supported on an internal surface of the attachment assembly 23). In the embodiment of FIG. 4, certain enhancers may be used to improve the signal-to-noise ratio due to the longer optical path between the light source, sensor and reflective surface. For example a stronger light source 32 or more sensitive optical sensor 34 may be used. The enhancers may alternatively or additionally be implemented as one or more collector lenses to focus the light beam and/or baffles at the sensor 34 to blind-out scattered light/radiation. The enhancers are however optional.

Figure 5:
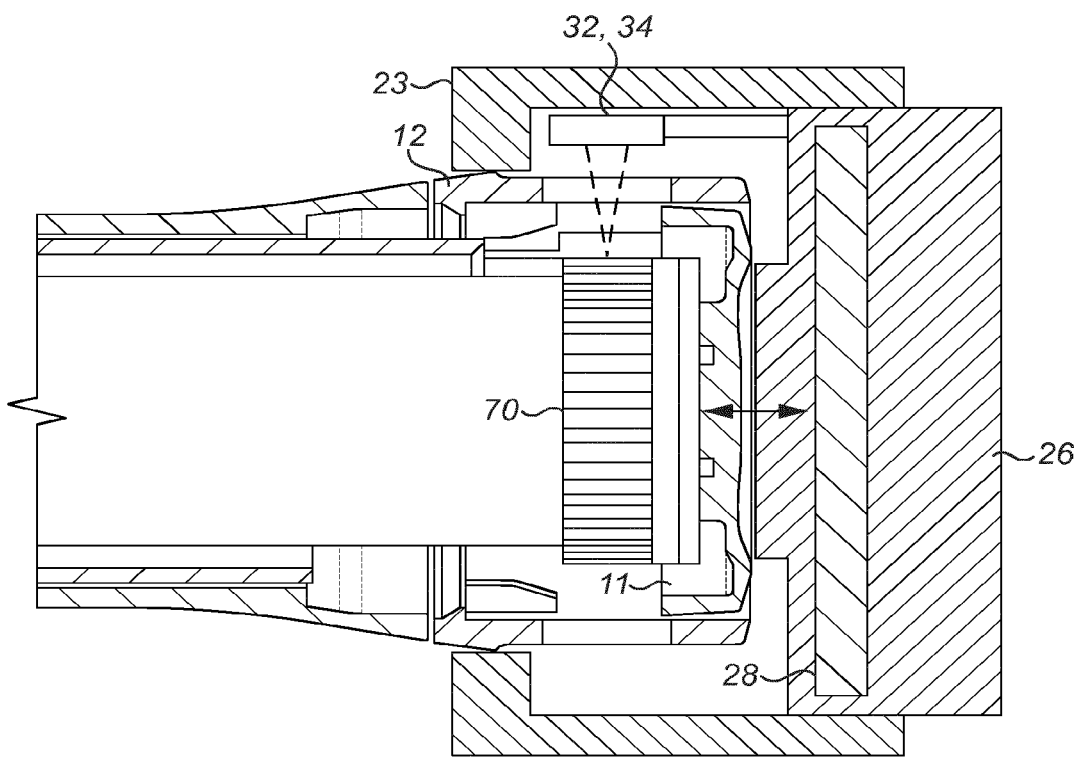
FIG. 5 illustrates a further alternative arrangement for the components of a data collection device.

FIG. 5 illustrates another alternative arrangement for the components of the data collection device 20. In this embodiment, the light source 32 and optical sensor 34 are supported in a recess between the dose setting dial 12 and an internal surface of the attachment assembly 23. For example, the light source 32 and optical sensor 34 may be supported on a protrusion of the electronics assembly 24. The attachment assembly 23 may have a recess to allow space for this protrusion. In this embodiment, the relatively reflective and non-reflective regions are disposed on an outer surface of the number sleeve 70, around the circumference. Such an arrangement may allow the reflective and non-reflective regions to be larger or spaced further apart as more space is available on this surface of the number sleeve 70. In this embodiment, the light path between the light source 32, reflective regions of the number sleeve 70 and optical sensor 34 passes through the dose setting dial 12. Therefore, at least the annular side wall of the dose setting dial 12 is partially or completely transparent to Infrared radiation. As can be appreciated from FIG. 5, the light path may also pass through a portion of the dose delivery button 11, since the dose delivery button 11 may extend into the dose setting dial 12 in order to connect with the dispensing mechanism of the injection device 1. Thus, this portion of the dose delivery button 12 may also be transparent to IR radiation.

This embodiment may allow the optical path to be minimized and to remain unchanged when the dose delivery button 11 is depressed. This adds to increased dose detection reliability. This embodiment also has a simple mechanical design and construction. The attachment assembly 23 of this embodiment may have a wider diameter compared to that of FIGS. 3 and 4 to allow room for the light source 32 and optical sensor 34. This may reduce the force needed by the user to rotate the dose setting dial 12 during dose dialing and therefore improve the ease of use for users with reduced dexterity.

Figure 10:
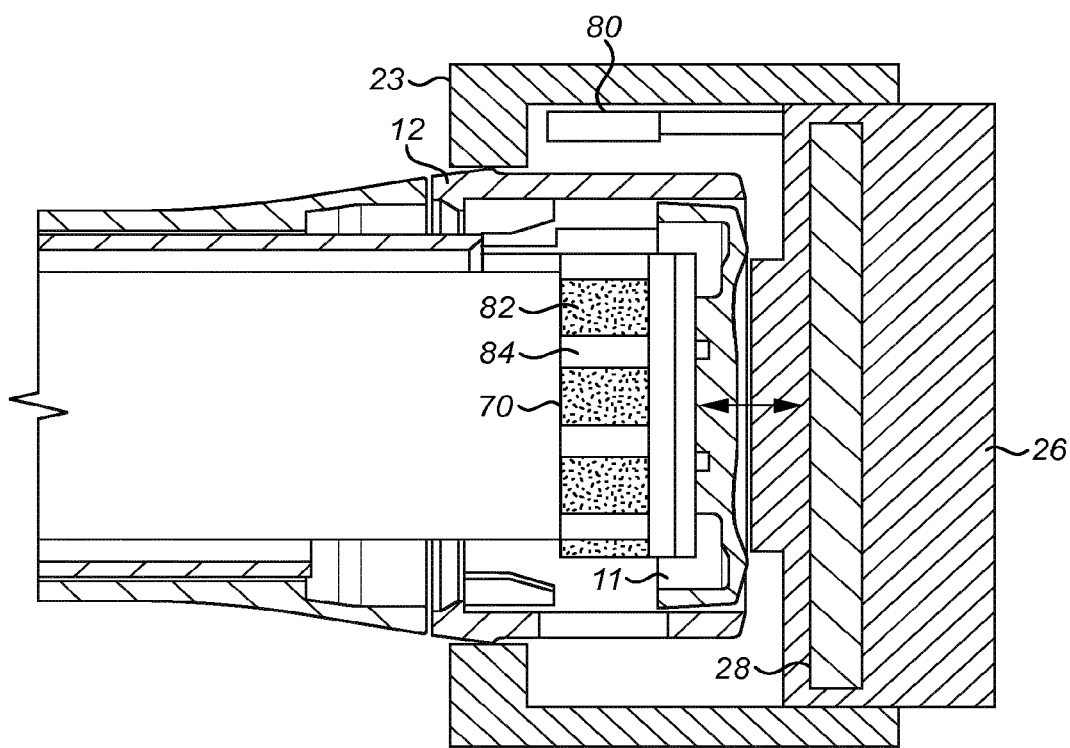
FIG. 10 illustrates a further alternative arrangement for the components of a data collection device.

Referring to FIG. 10, an alternative embodiment is shown. In this embodiment, instead of having a light source and optical sensor, the electronics assembly comprises a non-contact magnetic sensor 80, for example a Hall sensor. In this embodiment, the rotatable component 70 comprises a series of magnetic regions 82 and non-magnetic regions 84 spaced alternately around the circumference of the rotatable component 70. The magnetic regions 82 may be permanent magnets, such as regions containing magnetic particles or a magnetic ink. As the magnetic and non-magnetic regions, 82, 84, rotate past the magnetic sensor 80 during dose dispense, the magnetic sensor 80 detects a periodic change in the strength and optionally direction of the magnetic field. This information can then be used to determine the amount (angle) of rotating of the rotatable component 70. The dose setting dial 12 is transmissive or partially transmissive to the magnetic field generated by the magnetic regions 82, allowing the magnetic sensor 80 to detect rotation of the rotatable component 70 remotely and without the need for a cut-out or aperture in the dose setting dial 12. Although FIG. 10 shows the magnetic sensor 80 arranged radially relative to the dose setting dial 12, the magnetic sensor 80 may instead by located proximally of the dose setting dial 12, in the same manner as shown in FIGS. 3 and 4.

Figure 6:
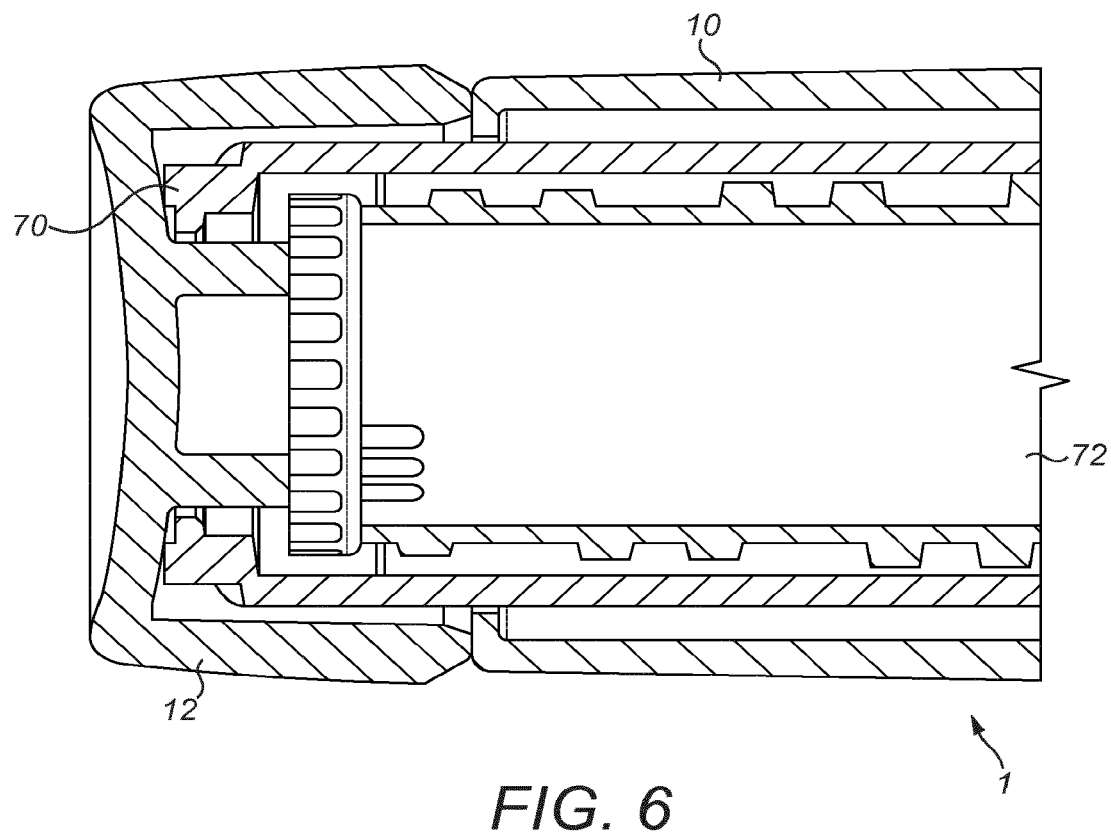
FIG. 6 is a cut-away view of a second type of injection device to which a data collection device may be attached.

FIG. 6 is a cut-away view of a second type of injection device 1 to which the data collection device 20 may be attached. In this embodiment, the injection device 1 has a dose setting dial 12 (also referred to herein as a dose selection element 12), but does not have a separate dose delivery button, e.g. the dose setting dial may also function as the dose delivery means when depressed.

The dose setting dial 12 is configured to be rotated to set a dose. This causes the dose setting dial 12 to move proximally out of the housing 10. When a dose is dispensed from the injection device 1, the dose setting dial 12 moves back (distally) into the housing but does not rotate. As with the embodiments described with respect to FIGS. 3-5, an internal component 70, such as a number sleeve 70, rotates during dose dispense. The data collection device 20 is configured so as to detect and measure the rotation of this internal component 70 when attached to the injection device 1. The injection device 1 shown in FIG. 6 may also have other components which rotate when a dose is dispensed, such as a drive sleeve 72. In the embodiment shown, the drive sleeve 72 has a series of crenellations at its proximal end. The relatively reflective regions may be printed or otherwise deposited directly onto the upper surfaces of these crenellations. In general, any component which is located close to the dose setting dial and which rotates when a dose is dispensed from the injection device 1 may be used as the internal component having the pattern of relatively reflective and non-reflective regions formed on a surface thereof.

Figure 7:
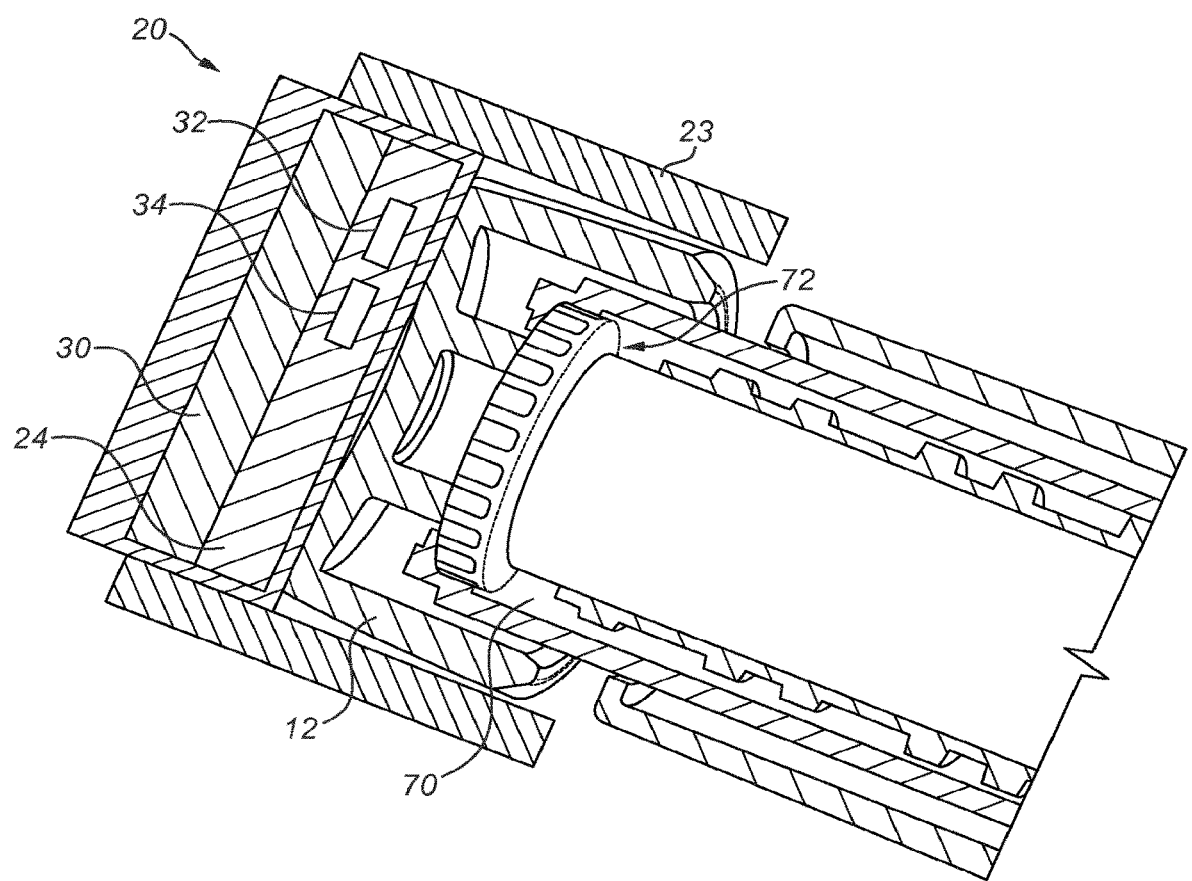
FIG. 7 shows a cross-sectional view of a data collection when attached to the injection device of FIG. 6.

FIG. 7 shows a cross-sectional view of the data collection device 20 according to some embodiments, when attached to the injection device 1 of FIG. 6. The data collection device 20 comprises an attachment assembly 23 and an electronics assembly 24, which may be integral or otherwise fixedly secured together. For example, the attachment assembly 23 may form part of a housing 21 of the data collection device 24, and the housing 21 may also retain the electronics assembly 24.

The attachment assembly 23 is configured to secure the data collection device 20 to the dose setting dial 12. As previously described, the data collection device 20 may employ a simple friction fit to releasably secure it to the dose setting dial 12 and the formations 71a, 71b, 71c on the dose setting dial 12 may be used to facilitate attachment or angular alignment.

When the data collection device 20 and injection device 1 are secured together, the electronics assembly 24 is configured to abut the dose setting dial 12. The data collection device 20 effectively replaces the dose setting dial, as the user interacts directly with the data collection device 20 in the same way as they would with the dose setting dial to set and deliver a dose of medicament.

The electronics assembly 24 comprises numerous components including a PCB 28, the light source 32, the optical sensor 34, a processor arrangement and a battery 30. In the embodiment shown in FIG. 7, the light source 32 and the optical sensor 34 are supported on the distal side of the electronics assembly 24 such that they are adjacent to the proximal end face of the dose setting dial 12. The light source 32 and sensor 34 are hence supported on a side of the data collection device which abuts the dose dial of the drug delivery device when attached thereto.

In these embodiments, the light source 32 is an Infrared light source and the optical sensor 34 is an Infrared optical sensor. The dose setting dial is transparent or substantially transparent to Infrared radiation. Thus the light emitted by the light source 32 passes through the dose setting dial and illuminates the internal components. In particular the number sleeve 70 is a hollow cylinder which extends to the proximal end of the housing 10 and moves longitudinally with the dose setting dial 12 when a dose is set. The number sleeve may be releasably fixed to the dose setting dial 12 such that the annular end surface of the number sleeve 70 is sits underneath the dose delivery button 11 and is illuminated by the Infrared light of the light source 32. The number sleeve 70 is provided with a pattern of relatively reflective and non-reflective regions on the annular end surface. For example, equally spaced and equally sized reflective and non-reflective sections may be arranged alternately. Alternatively, the drive sleeve 72 or another internal component may be provided with the pattern of relatively reflective and non-reflective regions.

During a dose dispensing operation, the light source 32 illuminates a portion of the number sleeve 70 including a portion of the pattern of relatively reflective and non-reflecting regions; and the optical sensor 34 receives the light reflected by at least the relatively reflective regions as they pass underneath. The output of the optical sensor 34 is relayed to the processor 50 which calculates an amount of rotation of the number sleeve 70 during the dose dispensing operation. From the amount of rotation, the delivered dose can be calculated. This may be done by the data collection device or by another computing device.

In general it is necessary to know the type of the injection device 1 to which the data collection device 20 is attached in order to determine a dose of medicament which has been dispensed. Therefore, in some embodiments, the data collection device 20 measures only the amount of rotation of the internal component in degrees. This information is saved in a memory of the data collection device 20 and may be communicated by the data collection device 20 to an external computing device where it is combined with information about the type of injection device 1 in order to record the delivered medicament dose.

Similar to the embodiment described above with reference to FIG. 5, the light source 32 and optical sensor 34 may instead be supported in a recess between the dose setting dial 12 and an internal surface of the attachment assembly 23. For example, the light source 32 and optical sensor 34 may be supported on a protrusion of the electronics assembly 24. The attachment assembly 23 may have a recess to allow space for this protrusion. In such embodiments, the relatively reflective and non-reflective regions are disposed on an outer surface of the number sleeve 70, around the circumference. This may have the advantage over the previously described embodiments of allowing the reflective and non-reflective regions to be larger or space further apart as more space is available on this surface of the number sleeve 70. In these embodiments, the light path between the light source, reflective regions of the number sleeve and optical sensor passes through the annual side wall of the dose setting dial 12, which is partially or completely transparent to Infrared radiation. In all of the embodiments, the light source 32 and the optical sensor 34 are supported on a part of the data collection device which abuts the dose dial 12 (which may include a dose delivery button 11) of the drug delivery device 1 either radially or proximally when attached thereto.

In a further alternative embodiment (not shown), the electronics assembly is integral with or supported on an internal surface of the attachment assembly 23 and is not configured to move relative to the attachment assembly. This is similar to the embodiment shown in FIG. 4. However, in this alternative, the light source 32 and optical sensor 34 may instead be supported on side of the electronics assembly 24 such that they are adjacent to the radial end face of the dose setting dial 12. This embodiment provides the benefits of having a simple mechanical design and enabling the reading of radial code.

The fixed construction and design of the embodiment of the data collection device 20 in FIG. 7 has the advantage of a simple mechanical construction (e.g., by minimizing relative movements) which provides an accurately defined positioning of optical sensor 34 relative to the injection device housing and the internal component including the pattern of relatively reflective and non-reflecting regions (e.g., dose dial 12) according to this embodiment.

A further alternative (not shown) is a modification of the embodiment shown in FIG. 7, however the light source 32 and optical sensor 34 are instead supported on a side of the electronics assembly 24 such that they are adjacent to the radial end face of the dose setting dial 12. This embodiment also provides a simple mechanical design and enables the reading of radial codes.

The data collection device of the present disclosure attaches directly to the dose setting dial of the medicament administration device. Previous data collection devices have attached to the main housing of the medicament administration device. This can impede the use of the medicament administration device by a user. Many such devices attach over a dose indication window in the housing of the medicament administration device. This obscures the dose indication window, making the user wholly reliant on the data collection device to indicate the dialed dose, which may reduce user confidence in the medicament administration device. Some other such devices require an additional cut out or aperture in the housing of the medicament administration device in order to view or connect with an internal moveable component. Cutting out a part in the housing of the medicament administration device makes the ingress of dust and dirt inside the delivery mechanism more likely. It may also present problems relating to the sterility of the medicament administration device.

The data collection device of the present disclosure is able to monitor the amount of medicament dispensed from the medicament administration device remotely, without contacting or being secured to the main housing of the medicament administration device. The data collection device is configured to attach to and to effectively replace the part of the medicament administration device with which the user would normally interact. When a user wishes to dial a dose, they grasp and rotate the housing 21 of the data collection device 20 which in turn rotates the dose setting dial 12. The user can continue to observe the mechanical dose indication window 13 of the medicament administration device. When the user wishes to inject a dose, they exert a force on the proximal end of the data collection device. This in turn communicates a force to the dose setting dial. Where the medicament administration device has a dose delivery button 11, the button 26 of the data collection device is configured to depress relative to the housing 21 and therefore to depress the dose delivery button 11 in turn. Therefore a user would notice no material difference in the way in which they operate the medicament administration device as a result of the addition of the data collection device according to the present invention.

The data collection device of the present disclosure may use infrared light as an illumination source. This allows the external components of the medicament administration device to be made out of a plastic or other material which is opaque to optical wavelengths, but transparent or partially transparent to Infrared wavelengths. No additional cut out, aperture or the like are required, although only the appropriate areas of the medicament administration device may be made of the IR transmissive material, effectively forming an Infrared 'window'.

The relatively reflective and non-reflective regions of the pattern may be printed, deposited, etched or otherwise created directly onto the number sleeve 70 or other suitable internal component during that component's manufacture. In some examples, the internal component is located in close proximity to the dose setting dial. The medicament administration device may then be assembled in the same way as before, using the same assembly method and tools. Therefore, only very minimal modification of the medicament administration device design and creation may be required in order to implement the invention.

As discussed above in relation to FIG. 10, the light source 32 and optical sensor 34 in FIG. 7 may instead be replaced with a magnetic sensor 80. The relatively reflective and non-reflective regions of the pattern on the rotatable component 70 may be replaced by alternating magnetic regions 82 and non-magnetic regions 84 such that when the rotatable component 70 is rotated during a dose dispensing operation, there is a periodic change in the magnetic field detected by the magnetic sensor 80.

Figure 8:
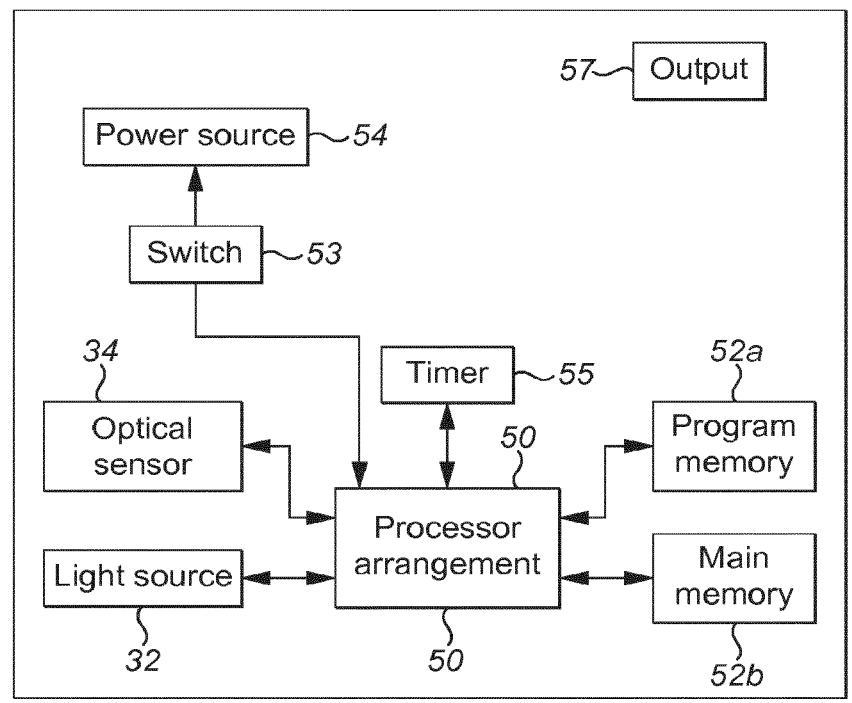
FIG. 8 is a block diagram of the data collection device.

FIG. 8 is a block diagram of the data collection device 20. The data collection device 20 includes a processor arrangement 50 including one or more processors, such as a microprocessor, a Digital Signal Processor (DSP), Application Specific Integrated Circuit (ASIC), Field Programmable Gate Array (FPGA) or the like, together with memory units 52a, 52b, including program memory 52a and main memory 52b, which can store software for execution by the processor arrangement 50. The data collection device includes the Infrared light source 32 and the Infrared optical sensor 34. The processor arrangement 50 controls operation of the light source 32 and the optical sensor 34 and receives signals from the optical sensor 34.

The data collection device 20 has a power source 54 which may be a battery, for example a coin cell. The data collection device 20 may optionally include a switch 53 configured to be triggered when or shortly before a dose is dispensed. To this end, the switch 53 may include a pressure or touch sensitive area in the end plate 22 or button 26 of the data collection device 20, for example a piezoelectric switch. The switch 53 may control application of power from the power source 54 to the processor arrangement 50 and other components of the data collection device 20. In embodiments in which the electronics assembly 24 and attachment assembly 23 are configured to move longitudinally relative to each other, the switch 53 may be implemented mechanically. For example, electrodes may be disposed on an internal surface of the attachment assembly 23 and corresponding electrodes on the electronics assembly 24 may make contact (and hence complete a circuit) when the button 26 is depressed. This may then trigger the wake-up of the other electronics, including the light source and optical sensor.

Alternatively, the wake-up switch may be implemented optically as an "optical wake-up sensor". In particular, the dose delivery button 11 of the injection device 1 may be coloured, for example green, while the underlying rotatable component 70 may be white (or black). When the dose delivery button 11 is depressed, it moves in front of the optical wake-up sensor and the change in reflectance and/or colour can be detected, providing the wake-up signal for the other electronics. This change in reflectance or colour can also be used to determine the start and end times of an injection process. In this case a switch as described before may function to wake-up the electronics, including the light source and optical sensor and an optical switch may use the change in reflectance or colour to determine start and end times of an injection process. This could be helpful in determining if an injection process has occurred or if a priming process has occurred. Further, the colour/reflectance switch could be used to determine how long the button has been pressed and use this to see if a dwell time has been respected by the user.

A timer 55 is also included. The processor arrangement 50 may use the timer 55 to monitor a length of time that has elapsed since an injection was completed, determined using the switch 53. Also optionally, the processor arrangement 50 may compare the elapsed time with a predetermined threshold, to determine whether a user may be attempting to administer another injection too soon after a previous injection and, if so, generate an alert such as an audible signal and/or generate an optical signal such as blinking one or more LEDs. The data collection device 20 may comprise a number of LEDs or other light sources for providing optical feedback to a user. For example, the LEDs may use different colours and/or lighting patterns such as blinking with constant or changing periodicity. On the other hand, if the elapsed time is very short, it may indicate that the user is administering a medicament amount as a "split dose", and the processor arrangement 50 may store information indicating that a dosage was delivered in that manner. In such a scenario the elapsed time is compared with a predetermined threshold in the range of a few seconds, e.g. 10 seconds up to a few minutes, e.g. 5 minutes. According to an example the predetermined threshold is set to 2 minutes. If the time elapsed since the last injection is two minutes or less, the processor arrangement 50 stores information indicating that the dosage was delivered as a "split dose".

Another optional purpose for monitoring the elapsed time by the processor arrangement 50 is to determine when the elapsed time has passed a predetermined threshold, suggesting that the user might have forgotten to administer another injection and, if so, generate an alert.

The processor is further configured to store data relating to date and/or time information, data relating to information from the optical sensor 34, or combinations thereof. In particular, the memory is configured to store a combination of date and/or time information and internal component rotation information retrieved from the optical sensor 34 output data. In this way the memory is able to store a log that provides a history of information on number sleeve 70 (or other internal component) rotation. Data can for example be stored in the main memory 52b. Alternatively, data may be stored is a separate data storage section (not shown) of the memory.

Since the number sleeve or other internal component rotates as medicament is expelled from the injection device 1, the angle of rotation measured by the optical sensor 34 is proportional to the amount of medicament expelled. It is not necessary to determine a zero level or an absolute amount of medicament contained in the injection device 1. In this way the sensor arrangement is less complex than compared to a sensor arrangement that is configured for absolute position detection. Moreover, since it is not necessary to monitor the numbers or tick marks on the number sleeve 70 displayed through the dosage window 13, the data collection device 20 may be designed so that it does not obscure the dosage window 13.

Figure 9:
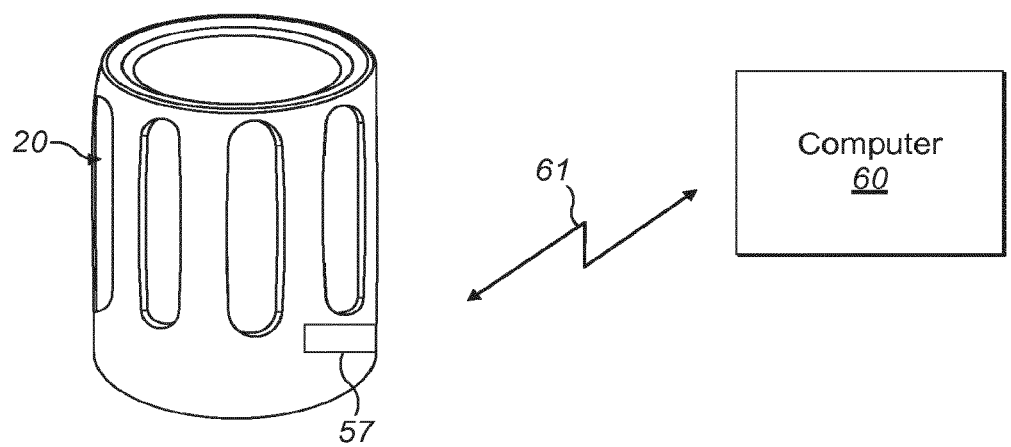
FIG. 9 shows a system in which the data collection device is connected to another device, such as a personal computer.

An output 57 is provided, which may be a wireless communications interface for communicating with another device via a wireless network such as wi-fi, Bluetooth®, or NFC, or an interface for a wired communications link, such as a socket for receiving a Universal Series Bus (USB), mini-USB or micro-USB connector. FIG. 9 depicts an example of a system in which the data collection device 20 is connected to another device, such as a personal computer 60, via a wireless connection 61 for data transfer. Alternatively or in addition, the data collection device 20 may be connected to another device via a wired connection. For example, the processor arrangement 50 may store determined number sleeve 70 rotation angles and time stamps (including date and/or time) for the injections as they are administered by the user and subsequently, transfer that stored data to the computer 60. The computer 60 may be configured to calculate an administered dose based on further information entered by the user or a medical professional regarding the type of injection device and the type of medicament. The computer 60 maintains a treatment log and/or forwards treatment history information to a remote location, for instance, for review by a medical professional.

According to some embodiments, the data collection device 20 may be configured to store data such as number sleeve 70 rotation angles and time stamps of up to 35 injection events. According to a once-daily injection therapy this would be sufficient to store a treatment history of about one month. Data storage is organized in a first-in first-out manner ensuring that most recent injection events are always present in the memory of the data collection device 20. Once transferred to a computer 60 the injection event history in the data collection device 20 will be deleted. Alternatively, the data remains in the data collection device 20 and the oldest data is deleted automatically once new data is stored. This way the log in the data collection device is built up over time during usage and will always comprise the most recent injection events. Alternatively, other configuration could comprise a storage capacity of 70 (twice daily), 100 (three months) or any other suitable number of injection events depending on the therapy requirements and/or the preferences of the user.

In another embodiment, the output 57 may be configured to transmit information using a wireless communications link and/or the processor arrangement 23 may be configured to transmit such information to the computer 60 periodically.

The specific embodiments described in detail above are intended merely as examples of how the present invention may be implemented. Many variations in the configuration of the data collection device 20 and/or the injection device 1 may be conceived.

In particular, while the embodiments above have been described in relation to collecting data from an insulin injector pen, it is noted that embodiments of the disclosure may be used for other purposes, such as monitoring of injections of other medicaments. Although the data collection device has been described primarily as comprising a single Infrared light source 32, the data collection device may comprise a plurality of light sources 32. The plurality of light sources 32 may be supported at different positions on the electronics assembly 24 and/or the attachment assembly 23 and may be angled and or focused so as to illuminate a particular part of the internal component 70 from a particular angle when the data collection device is attached to the dose setting dial.

In some implementations, the data collection device 20 includes a display (not shown), which could for example occupy the end plate 22 of the data collection device 20. Various information can be displayed, such as the length of time that has elapsed since an injection was completed, and warning messages where a user is attempting to administer another injection too soon after a previous injection.

The invention claimed is:

1. A data collection device comprising:
an attachment assembly for attaching the data collection device to a dose setting dial of a medicament administration device, the dose setting dial disposed at a proximal end of the medicament administration device;
a light source configured to illuminate a portion of an internal component of the medicament administration device, the internal component comprising a plurality of reflective regions formed on the internal component; and
an optical sensor configured to receive light reflected by the plurality of reflective regions,
wherein the light source and optical sensor are configured to be located proximally of the dose setting dial when the data collection device is attached to the dose setting dial such that a light path between the light source, internal component, and optical sensor passes through a proximal end surface of the dose setting dial.

2. The data collection device according to claim 1, wherein the light source and the optical sensor are supported on a part of the data collection device configured to abut the dose setting dial of the medicament administration device.

3. The data collection device according to claim 1, wherein the attachment assembly is configured to releasably attach the data collection device to the dose setting dial of the medicament administration device.

4. The data collection device according to claim 1, wherein the dose setting dial of the medicament administration device is at least partially transmissive to electromagnetic radiation emitting by the light source.

5. The data collection device according to claim 4, wherein the electromagnetic radiation is infrared light.

6. The data collection device according to claim 1, wherein the data collection device comprises an electronics assembly comprising the light source and the optical sensor.

7. The data collection device according to claim 6, wherein the electronics assembly is configured to abut a dose delivery button of the medicament administration device when the data collection device is attached to the medicament administration device and to cause depression of the dose delivery button when the electronics assembly is moved longitudinally in a distal direction relative to the attachment assembly and wherein the light path between the light source, internal component and optical sensor passes through the dose delivery button.

8. The data collection device according to claim 6, wherein the electronics assembly and the attachment assembly are fixedly connected together.

9. The data collection device according to claim 8, wherein the electronics assembly is configured to abut the proximal end surface of the dose setting dial when the data collection device is attached to the dose setting dial.

10. The data collection device according to claim 1, wherein the data collection device comprises a processor arrangement configured to receive one or more signals from the optical sensor and to detect an occurrence of a medicament delivery from the medicament administration device.

11. The data collection device according to claim 10, wherein the processor arrangement is configured to detect occurrences of two separate medicament deliveries and to amalgamate the two separate medicament deliveries when it is determined that the two separate medicament deliveries occurred within a predetermined time of each other.

12. The data collection device according to claim 10, wherein the processor arrangement is configured to determine, from the one or more signals received from the optical sensor, an amount of rotation of the internal component.

13. The data collection device according to claim 10, wherein the data collection device further comprises a switch configured to be triggered by application of a force to a proximal end of the data collection device and wherein the switch is configured to, in response to being triggered, cause activation of at least the light source, optical sensor, and processor arrangement.

14. The data collection device according to claim 13, wherein the switch is an optical wake-up sensor configured to sense a reflectance and/or colour of an underlying component of the medicament administration device and to provide a wake-up signal when a change in the reflectance and/or colour is detected.

15. The data collection device according to claim 13, wherein the data collection device further comprises a timer, the switch is configured to trigger activation of the timer and wherein the data collection device is further configured to determine an elapsed time since the timer was last triggered and to generate an alert if the elapsed time is inconsistent with a threshold condition.

16. The data collection device according to claim 15, wherein the processor arrangement is configured to:
determine a time stamp for an administration of a medicament dosage using the timer and to store the determined medicament dosage and said time stamp and transmit a log of determined internal component rotation angles and time stamp information to another device.

17. A system comprising:
a medicament administration device comprising:
a dose setting dial disposed at a proximal end of the medicament administration device; and
an internal component that rotates around a longitudinal axis of the medicament administration device when a dose of medicament is delivered from the medicament administration device, wherein the internal component includes a plurality of reflective regions, and a data collection device comprising:
an attachment assembly for attaching the data collection device to the dose setting dial;
a light source configured to illuminate a portion of the internal component including the plurality of reflective regions; and
an optical sensor configured to receive light reflected by the plurality of reflective regions,
wherein the light source and optical sensor are located proximally of the dose setting dial when the data collection device is attached to the dose setting dial such that a light path between the light source, internal component, and optical sensor passes through a proximal end surface of the dose setting dial.

18. The system according to claim 17, wherein the light source and the optical sensor are configured to be supported on a part of the data collection device which abuts the dose setting dial of the medicament administration device.

19. The system according to claim 17, wherein the plurality of reflective regions comprises evenly spaced reflective regions formed on a proximal end surface of the internal component.

20. The system according to claim 17, wherein the light source and optical sensor are configured to be located between the attachment assembly and the dose setting dial when the data collection device is attached to the dose setting dial such that the light path between the light source, internal component, and optical sensor passes through the dose setting dial.

21. The system according to claim 20, wherein the light path between the light source, internal component, and optical sensor also passes through a part of a dose delivery button.

22. The system according to claim 20, wherein the internal component comprises a pattern of relatively reflective and non-reflecting regions, the pattern of relatively reflective and non-reflecting regions comprising evenly spaced relatively reflective and non-reflecting regions formed on the internal component.

23. The system according to claim 19, wherein the medicament administration device comprises a housing and wherein the dose setting dial is configured to not rotate relative to the housing when the dose of medicament is delivered from the medicament administration device.

24. The system according to claim 19, wherein the internal component comprises a plurality of equally spaced crenellations and wherein the reflective regions are formed on upper surfaces of the plurality of crenellations.

* * * * *